(12) United States Patent
Johnson et al.

(10) Patent No.: US 10,869,636 B2
(45) Date of Patent: Dec. 22, 2020

(54) MOBILE COMMUNICATION DEVICE TO SENSE AND COLLECT A USER'S DIAGNOSTIC INFORMATION

(71) Applicant: Motorola Mobility LLC, Chicago, IL (US)

(72) Inventors: McKay Robert Johnson, Chicago, IL (US); Thomas Andrew Annett, Barrington, IL (US); Andy Kuo-Yuan Baw, Barrington, IL (US)

(73) Assignee: Motorola Mobility LLC, Chicago, IL (US)

( * ) Notice: Subject to any disclaimer, the term of this patent is extended or adjusted under 35 U.S.C. 154(b) by 418 days.

(21) Appl. No.: 15/793,404

(22) Filed: Oct. 25, 2017

(65) Prior Publication Data

US 2019/0117161 A1    Apr. 25, 2019

(51) Int. Cl.
| | |
|---|---|
| *A61B 5/00* | (2006.01) |
| *A61B 5/024* | (2006.01) |
| *A61B 5/021* | (2006.01) |
| *A61B 5/026* | (2006.01) |
| *G16H 40/63* | (2018.01) |
| *A61B 5/01* | (2006.01) |

(52) U.S. Cl.
CPC .......... *A61B 5/6898* (2013.01); *A61B 5/0017* (2013.01); *A61B 5/01* (2013.01); *A61B 5/021* (2013.01); *A61B 5/026* (2013.01); *A61B 5/02444* (2013.01); *G16H 40/63* (2018.01)

(58) Field of Classification Search
CPC ....... A61B 5/6898; A61B 5/0017; A61B 5/01; A61B 5/021; A61B 5/02444; A61B 5/026; G16H 40/63
USPC ......................................................... 600/301
See application file for complete search history.

(56) References Cited

U.S. PATENT DOCUMENTS

| | | | |
|---|---|---|---|
| 2014/0077946 A1* | 3/2014 | Tran ...................... | A61B 5/1112 340/539.13 |
| 2015/0164349 A1* | 6/2015 | Gopalakrishnan ..... | A61B 5/746 600/508 |

* cited by examiner

*Primary Examiner* — Aaron F Roane
(74) *Attorney, Agent, or Firm* — SBMC (57) ABSTRACT

Various embodiments provide a mobile communication device to sense and collect a user's diagnostic information. A deployable platform mounted on the mobile communication device, receives touch input from a user's finger. At least one sensor mounted on the deployable platform is used to sense one or more properties associated with the touch input. Diagnostic information associated with the one or more touch input properties is collected and a notification describing the diagnostic information is provided using the mobile communication device.

20 Claims, 11 Drawing Sheets

MOBILE COMMUNICATION DEVICE TO SENSE AND COLLECT A USER'S DIAGNOSTIC INFORMATION

BACKGROUND

As technology continues to advance, challenges are posed to those who develop and manufacture mobile devices to continue to provide better and different technology options to consumers.

For example, many devices that are utilized to sense and collect a user's diagnostic information are large and cumbersome to move and/or are semi-permanently located at a health care professional's office so as to be inaccessible to most users unless the users physically visit the health care professional's office. These devices also typically include multiple cables, wires, ports, adapters, and/or accessories to obtain the diagnostic information. Moreover, these devices typically require manual recording of the diagnostic information, thus making collection of diagnostic information more susceptible to human error.

BRIEF DESCRIPTION OF THE DRAWINGS

Embodiments for a mobile communication device to sense and collect a user's diagnostic information are described with reference to the following Figures. The same numbers may be used throughout to reference like features and components that are shown in the Figures.

DETAILED DESCRIPTION

Overview

Various embodiments provide a mobile communication device to sense and collect a user's diagnostic information. Mobile communication devices include, by way of example and not limitation, smart phones, smart devices, IoT (Internet of Things) devices such as wearables such as smart watches, and the like. The mobile communication device provides an ergonomically-balanced mobile device that is free of excessive parts and pieces and which is intuitive to operate. Furthermore, diagnostic information is automatically collected by the mobile communication device where it can be processed locally and/or provided or otherwise transmitted, by way of a suitably-configured network, to one or more third-party service providers for further diagnostic analysis.

The mobile communication device can include a variety of sensors to measure various diagnostic information associated with the user. These sensors can include, by way of example and not limitation, heart rate sensors, blood oxygen sensors, blood pressure sensors, temperature sensors, and the like. In operation, the sensors are located on a deployable platform located on the back of the mobile communication device. The deployable platform is deployably mounted relative to the mobile communication device. In some embodiments, the deployable platform is rotatably mounted relative to the mobile communication device and is rotatable from an undeployed or stowed position, to a deployed position. The deployable platform can, however, be mounted in other ways such as being slidably mounted or otherwise mechanically coupleable/de-coupleable relative to the mobile communication device.

In the rotatable embodiment, when in the undeployed or stowed position, the deployable platform is received within a recessed well that is sized to ensure that the deployable platform is protected from things such as inadvertent snags and the like. In the deployed position, the deployable platform is rotated out of the recessed well to extend generally away from the mobile communication device. When in the deployed position, the deployable platform can be engaged by a user, as by being placed against the user's finger, so that the sensors on the deployable platform can collect diagnostic information associated with the user. In at least some embodiments, the deployable platform is dimensioned in such a way that it can be "scissor-gripped" between a user's two fingers.

In at least some embodiments, the sensors and related componentry that implement the diagnostic sensing can be integrated as part of the mobile communication device. That is, such sensors and related componentry can be included within the housing of the communication device and can comprise an integral part of the mobile communication device. Alternately or additionally, such sensors and related componentry can be included in a modular attachment which may be detachably connected to the mobile communication device. In these instances, the modular attachment can communicate with the mobile communication device through a suitably-configured hardware interface.

The various embodiments described herein thus provide a robust collection of functionality contained in a mobile communication device. By enabling sensing and collection of a user's diagnostic information, the embodiments can promote the health and physical fitness of the user by enabling the user to gather timely data and information concerning their health. In at least some instances, the data and information gathered by the mobile device can be provided to a third-party service provider for further analysis and evaluation. Results of the analysis and evaluation can be conveyed back to the mobile communication device and the user can be notified of the results. This can greatly reduce the amount of time that a user must wait for an evaluation and the associated results.

While features and concepts for sensing and collecting a user's diagnostic information can be implemented in any number of different devices, systems, environments, and/or configurations, embodiments for sensing and collecting a user's diagnostic information are described in the context of the following example devices, systems, and methods.

Example Operating Environment

Figure 1:
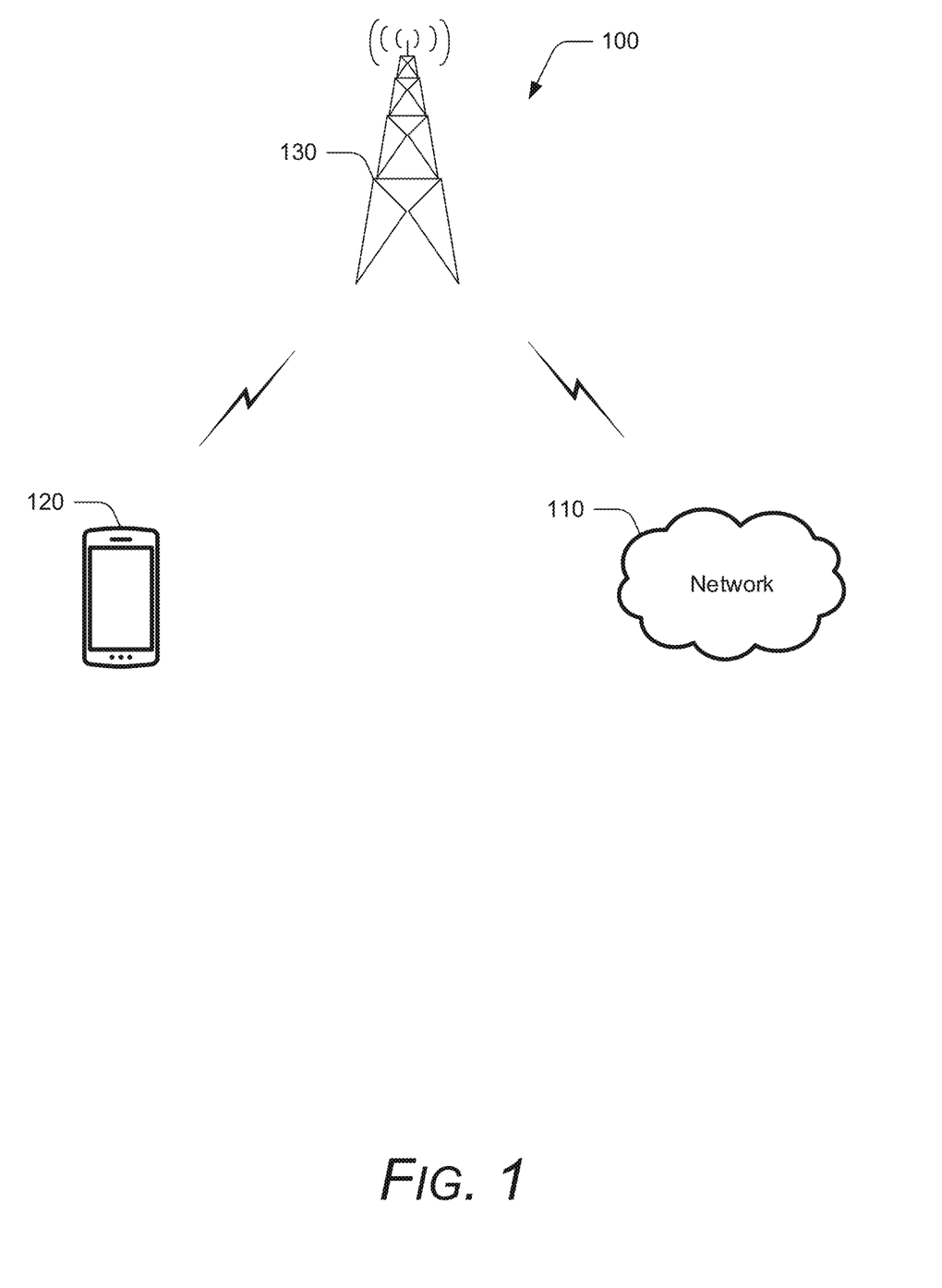
FIG. 1 illustrates an example operating environment in accordance with one or more embodiments.

FIG. 1 is an example block diagram of a system 100 according to one or more embodiments. The system 100 can include a network 110, a terminal 120, and a base station 130. The terminal 120 may be a wireless communication device, such as a mobile communication device, a personal digital assistant, and the like. The network 110 may include any type of network that is capable of sending and receiving signals, such as wireless signals. For example, the network 110 may include a wireless telecommunications network, a cellular telephone network, a Time Division Multiple Access (TDMA) network, a Code Division Multiple Access (CDMA) network and other like communications systems. In operation, the terminal 120 can communicate with the network 110 and with other devices on the network 110 by sending and receiving wireless signals via the base station 130.

Mobile Communication Device to Sense and Collect Diagnostic Information

Figure 2:
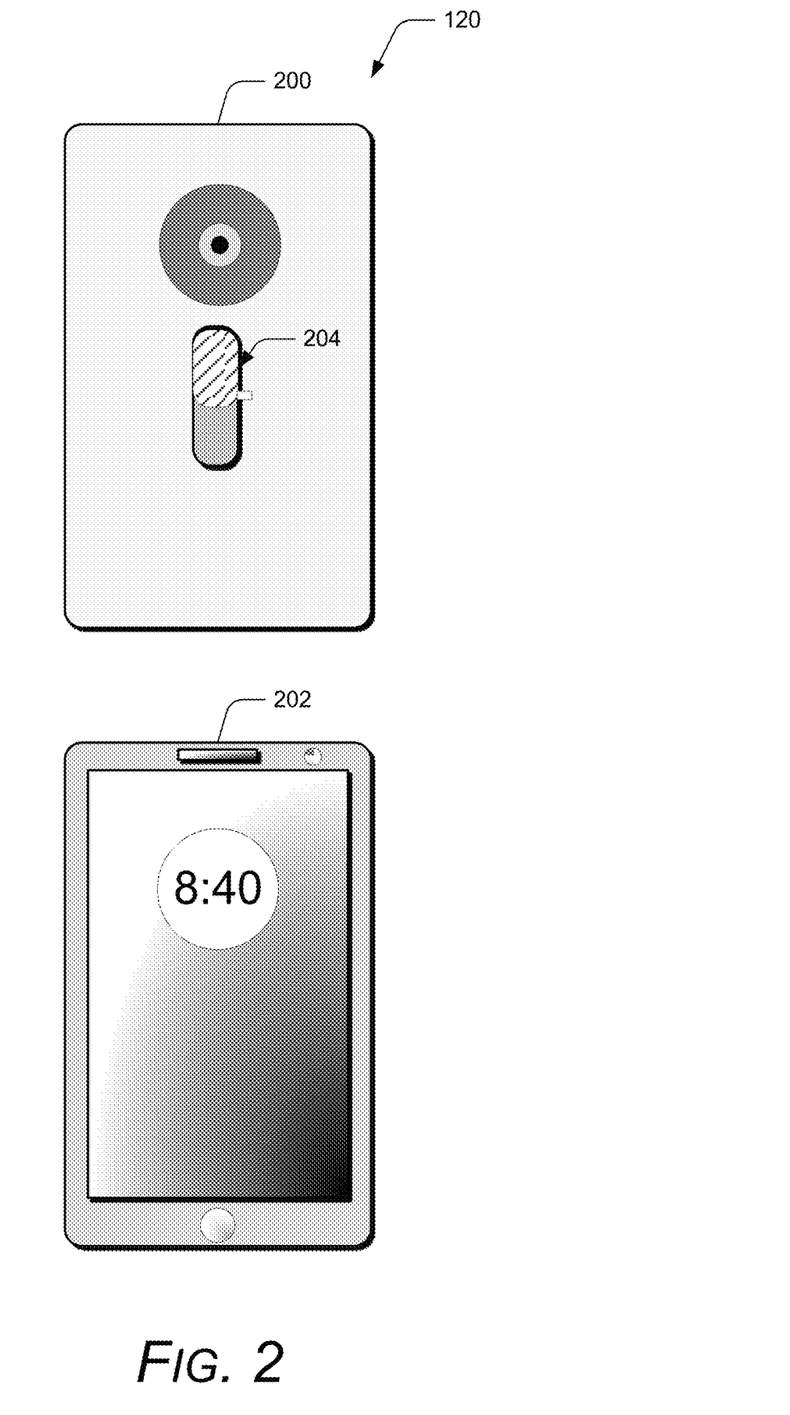
FIG. 2 illustrates an example terminal in the form of a mobile communication device in accordance with one or more embodiments.

FIG. 2 illustrates an example terminal 120 in the form of a mobile communication device. A view of the backside of the mobile communication device is shown at 200, and a view of the front side of the mobile communication device is shown at 202. The mobile communication device 120 includes a variety of sensors to measure various diagnostic information associated with the user. These sensors can include, by way of example and not limitation, heart rate sensors, blood oxygen sensors, blood pressure sensors, temperature sensors, and the like. In operation, the sensors are located on a deployable platform 204 (shown in cross-hatched form) located on the back of the mobile communication device. The deployable platform 204 is shown in more detail in FIGS. 2A and 2B. FIG. 2B is a view taken along line 2B-2B in FIG. 2A.

Figure 2A:
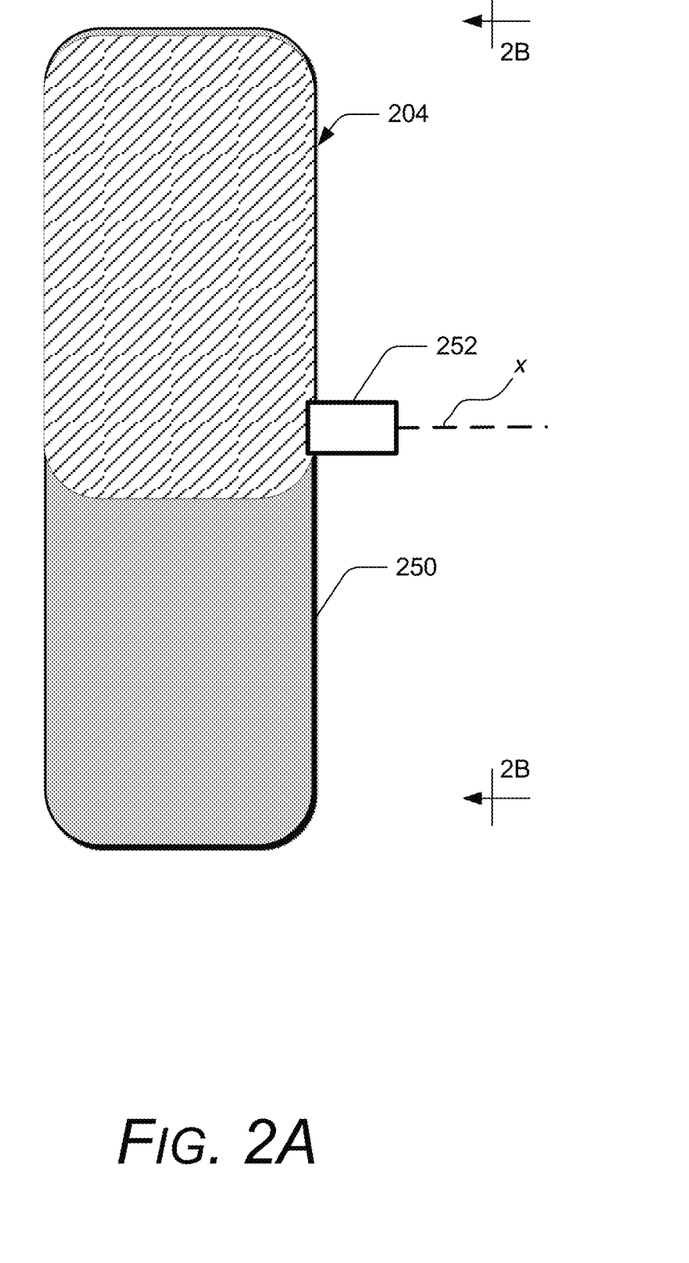
FIG. 2A illustrates a top plan view of an example deployable platform that can be operably associated with a terminal in the form of a mobile communication device in accordance with one or more embodiments.
Figure 2B:
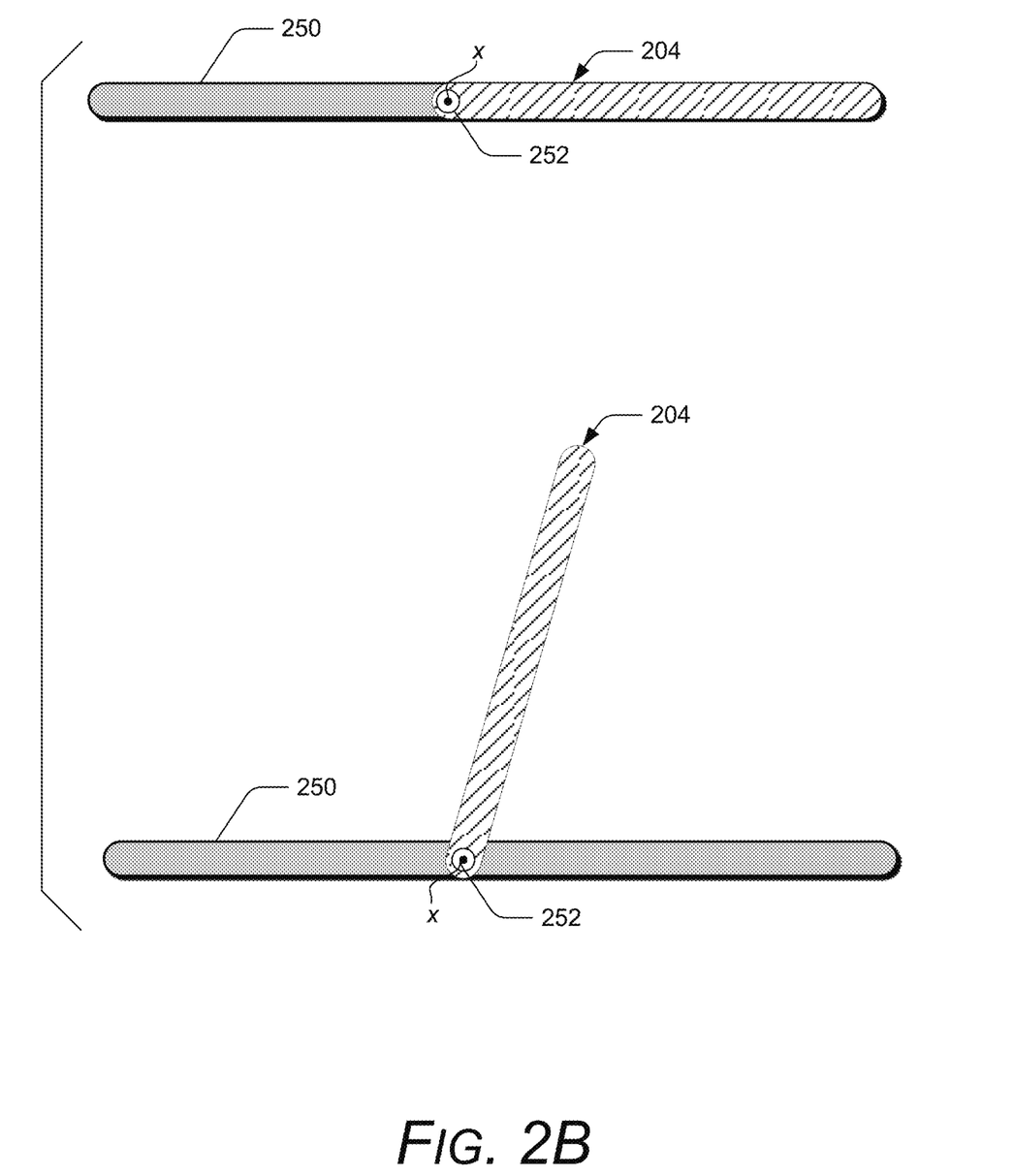
FIG. 2B illustrates side elevational views of a deployable platform, taken along line 2B-2B in FIG. 2A, in an undeployed state and in a deployed state, in accordance with one or more embodiments.

The deployable platform 204 is received within a well 250 and is rotatably mounted within the well 250 by way of a hinge structure 252 which permits rotatable deployment about the x axis, shown by the dashed line in FIG. 2A, relative to the mobile communication device. As shown in FIG. 2B, the deployable platform 204 is rotatable from an undeployed or stowed position (top most view), to a deployed position (bottommost view). In the undeployed or stowed position, the deployable platform is received within recessed well 250 that is sized to ensure that the deployable platform 204 is protected from things such as inadvertent snags and the like. In the deployed position, the deployable platform 204 is rotated, either manually, mechanically, or automatically, out of the recessed well 250 to extend generally away from the mobile communication device. When in the deployed position, the deployable platform can be engaged by a user, as by being placed against the user's finger, so that the sensors on the deployable platform can collect diagnostic information associated with the user. In at least some embodiments, the deployable platform is dimensioned in such a way that it can be "scissor-gripped" between a user's two fingers, as shown below in more detail.

Once the diagnostic information is collected, the diagnostic information can be analyzed and reported to the user. Analysis can take place either on the mobile communication device 120 or remote from the mobile communication device, as by a third-party provider. In the latter instance, the information or data can be transmitted by the mobile communication device 120 over network 110 (FIG. 1) to the third-party provider. Once the third-party provider has analyzed the diagnostic information, the results can then be reported back to the user and displayed on the mobile communication device 120.

Figure 3:
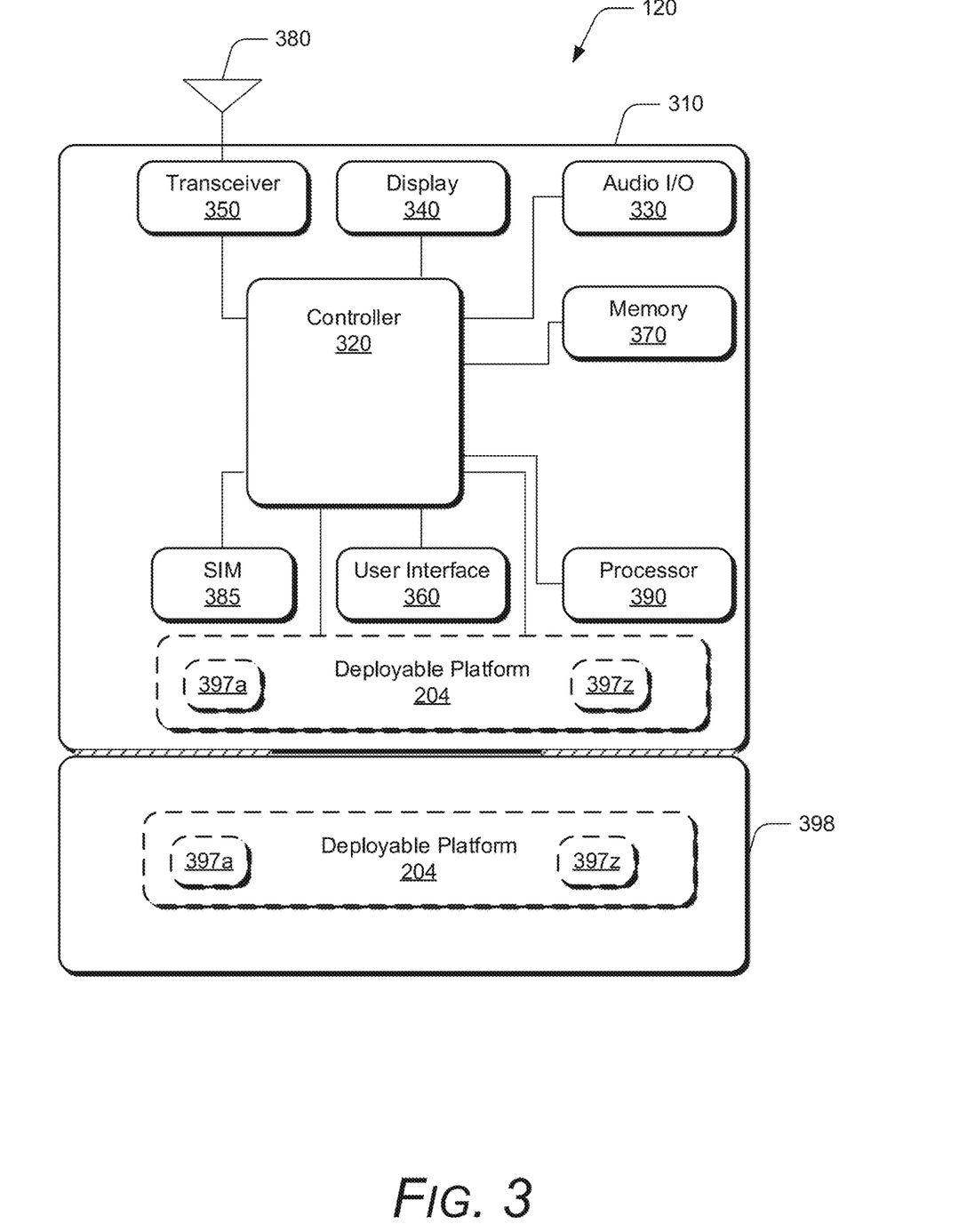
FIG. 3 illustrates a block diagram of an example mobile communication device in accordance with one or more embodiments.

FIG. 3 is an example block diagram of a mobile communication device 120 in accordance with one or more embodiments. The mobile communication device 120 can include a housing 310, a controller 320 coupled to the housing 310, audio input and output circuitry 330 coupled to the housing 310, a display 340 coupled to the housing 310, a transceiver 350 coupled to the housing 310, a user interface 360 coupled to the housing 310, memory 370, an antenna 380 coupled to the housing 310 and the transceiver 350, and a subscriber identification module 385 coupled to the controller 320. The mobile communication device 120 also includes a processor 390 connected to controller 320. The mobile communication device 120 depicted in FIG. 3 can be used to implement all the embodiments described in this document.

In addition, mobile communication device 120 can include a deployable platform 204 which, in turn, can include can include or otherwise be operably connected to one or more sensors, here represented by sensors 397a-397z. The sensors and deployable platform are shown in dashed lines because, as noted above, the sensors and deployable platform may optionally be integral to the mobile communication device 120, e.g., form part of the mobile communication device as manufactured and sold.

Alternately or additionally, these components may reside in a modular attachment, such as modular attachment 398, that is attached to the mobile communication device 120 and communicatively linked to components of the mobile communication device by way of a suitable interface, such as a hardware interface. An example modular attachment is Lenovo's Moto Mod, although other modular attachments may be employed.

Such modular attachment attaches to the mobile communication device using strong magnetic coupling elements, represented in the illustration as two crosshatched coupling elements between the housing 310 and modular attachment 398. A hardware interface (not specifically illustrated) between the modular attachment 398 and the mobile communication device 120 enables information and data to be exchanged between the modular attachment and the mobile communication device. So, for example, if sensors 397a-z reside in the modular attachment 398, information and data gathered by the modular attachment can be conveyed to the mobile communication device 120 by way of the hardware interface. This information and data can then, in at least some embodiments, be conveyed by the mobile communication device 120 to a third-party service provider for further analysis, or simply stored, analyzed and/or maintained for future use.

In the illustrated and described embodiment, the controller 320 is connected to various components within the mobile communication device 120 and is configured to organize, manage, and oversee processing that takes place on the mobile communication device. This includes serving as an interface to the various illustrated components to process information and data received from the components.

The audio input and output circuitry 330 can include a microphone, a speaker, a transducer, or any other audio input and output circuitry. The display 340 can be a liquid crystal display (LCD), a light emitting diode (LED) display, a plasma display, or any other means for displaying image and information. The transceiver 350 may include a transmitter and/or a receiver. The user interface 360 can include a hard or soft keypad, buttons, a touch pad, a joystick, an additional display, or any other device useful for providing an interface between a user and an electronic device. The memory 370 can include embedded memory such as a random access memory, a read only memory, etc. Memory 370 can include software code that is executable to implement various functionality on the mobile communication device.

The SIM 385 is an optional integrated circuit that stores information which is used to identify and authenticate subscribers on mobile telephony devices. It can also store contact information as well.

Processor 390 is configured to include a processing system of one or more processors (e.g., any of microprocessors, controllers, and the like) and/or a processor and memory system implemented as a system-on-chip (SoC) that processes computer-executable instructions. The processor system may be implemented at least partially in hardware, which can include components of an integrated circuit or on-chip system, an application-specific integrated circuit (ASIC), a field-programmable gate array (FPGA), a complex programmable logic device (CPLD), and other implementations in silicon and/or other hardware.

Sensors 397a-z can comprise any suitable type of sensors such as, by way of example and not limitation, heart rate and respiration rate sensors, blood oxygen sensors, blood pressure sensors, temperature sensors, and the like.

In one or more embodiments, the heart rate and respiration rate sensor can be implemented as photoplethysmography (PPG) sensor. A photoplethysmogram (PPG) is an optically obtained plethysmogram. A PPG is often obtained by using a pulse oximeter which illuminates the skin and measures changes in light absorption. A pulse oximeter can monitor the perfusion of blood to the dermis and subcutaneous tissue of the skin. With each cardiac cycle, the heart pumps blood to the periphery. Even though this pressure pulse is somewhat damped by the time it reaches the skin, it is enough to distend the arteries and arterioles in the subcutaneous tissue. If the pulse oximeter is attached without compressing the skin, a pressure pulse can be seen from the venous plexus, as a small secondary peak. The change in volume caused by the pressure pulse is detected by illuminating the skin with the light from a light emitting diode and then measuring the amount of light either transmitted or reflected to a photodiode. Each cardiac cycle appears as a peak. Because blood flow to the skin can be modulated by multiple other physiological systems, the PPG can also be used to monitor breathing (i.e., respiration rate) and other circulatory conditions.

In one or more embodiments, the blood oxygen sensor can be implemented as a pulse oximetry sensor. As noted above, pulse oximetry is a noninvasive method for monitoring a person's oxygen saturation or $SO_2$. In its transmissive application mode, a sensor device is placed on the thin part of a patient's body such as a fingertip. The device passes to wavelengths of light through the body part to a photo detector. It measures the changing absorbance at each of the wavelengths, allowing it to determine the absorbances due to the pulsing arterial blood alone.

In one or more embodiments, the blood pressure sensor can be implemented to utilize the principles of pulse wave velocity. Specifically, the velocity of the systolic pressure wave depends on a number of factors including stiffness of the arteries, i.e., arterial occlusion. Stiffness of the arteries, in turn, depends on many parameters including blood pressure. Therefore, the relationship between systolic blood pressure and pulse wave velocity can be utilized to ascertain a patient's blood pressure. Specifically, by measuring the time interval between two signals (ECG and PPG or PPG at two sites) a patient's blood pressure can be ascertained with reasonable accuracy.

In one or more embodiments, the temperature sensor can be implemented using infrared bolometry which enables temperature to be measured in a non-contact manner.

Having considered an example mobile communication device and its components in accordance with one or more embodiments, consider now an example modular attachment implementation in accordance with one or more embodiments.

Example Modular Attachment

Figure 4:
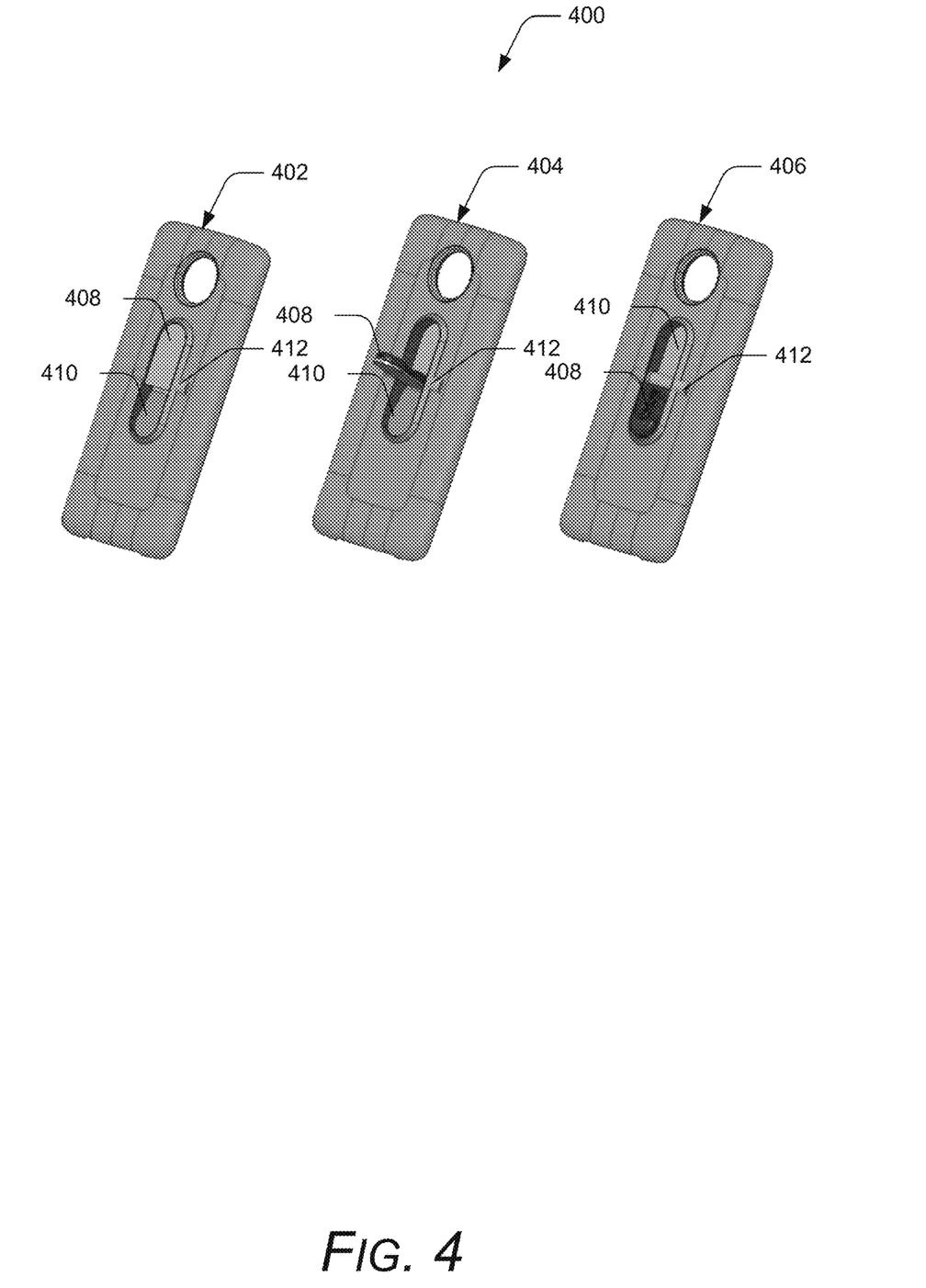
FIG. 4 illustrates a modular attachment for a mobile communication device in three different states in accordance with one or more embodiments.

FIG. 4 illustrates an example modular attachment in three different operational states, generally at 400. A first operational state 402 corresponds to a storage state. A second operational state 404 and a third operational state 406 correspond to different states in which a deployable platform 408 can be deployed from within a recessed well 410 for use as described below.

In the first operational state, the deployable platform 408 is received within well 410 and is rotatably mounted within the well 410 by way of a hinge structure 412 which permits rotatable deployment about the x axis, as described above, relative to a mobile communication device to which the modular attachment can be attached. The deployable platform 408 is rotatable from an undeployed or stowed position (operational state 402), to a deployed position (operational states 404, 406). In the undeployed or stowed position, the deployable platform is received within the recessed well 410 that is sized to ensure that the deployable platform 408 is protected from things such as inadvertent snags and the like. In the deployed position, the deployable platform 408 is rotated, either manually, mechanically, or automatically, out of the recessed well 410 to extend generally away from the mobile communication device. When in the deployed position, as in operational states 404, 406, the deployable platform 408 can be engaged by a user, as by being placed against the user's finger, so that the sensors on the deployable platform 408 can collect diagnostic information associated with the user. In at least some embodiments, the deployable platform is dimensioned in such a way that it can be "scissor-gripped" between a user's two fingers, as in operational state 404, which is shown in more detail in FIG. 5. In operational state 406, the deployable platform 408 is rotated to the opposite end of well 410 and can be used to measure a user's temperature as by having the user place their finger against an IR temperature sensor, an example of which is provided below.

Once the diagnostic information is collected, the diagnostic information can be analyzed and reported to the user. Analysis can take place either on the mobile communication device 120 or remote from the mobile communication device, as by a third-party provider. In the latter instance, the information or data can be transmitted by the mobile communication device 120 over network 110 (FIG. 1) to the third-party provider. Once the third-party provider has analyzed the diagnostic information, the results can then be reported back to the user and displayed on the mobile communication device 120.

Having considered an example modular attachment in accordance with one or more embodiments, consider now an example deployable platform, with sensors, in accordance with one or more embodiments.

Example Deployable Platform with Sensors

Figure 6:
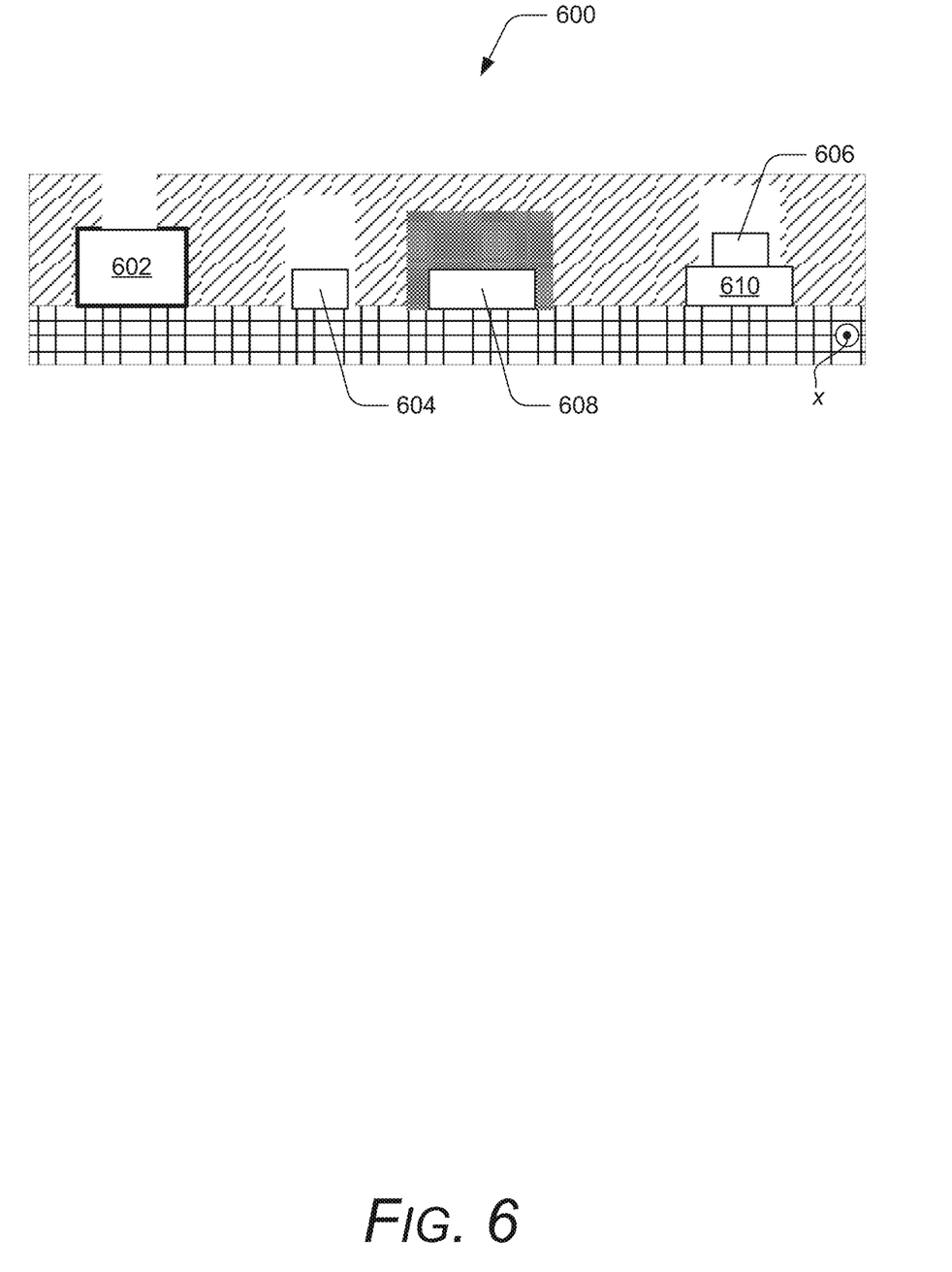
FIG. 6 illustrates components of an example deployable platform in accordance with one or more embodiments.

FIG. 6 illustrates an example deployable platform including multiple sensors, in accordance with one or more embodiments, generally at 600. In this particular example, deployable platform 600 includes a temperature sensor 602 in the form of an infrared bolometer to enable a user's temperature to be taken without requiring physical contact. In operation, the user places their finger adjacent the opening above sensor 602.

In addition to temperature sensor 602, deployable platform 600 includes an array of LEDs 604 and a corresponding photodiode 606 that is utilized for pulse oximetry and photoplethysmography measurements. A pressure sensor 608 is provided with a corresponding flexible membrane surrounding the pressure sensor to enable the deployable platform to ascertain when a user's finger is in contact with the deployable platform.

An interface ASIC 610 is provided to enable the deployable platform 600 to interface with the mobile communication device. It is to be appreciated and understood that the illustrated sensors are for example purposes only. Accordingly, other sensors and sensor types can be provided without departing from the spirit and scope of the claimed subject matter.

Figure 5:
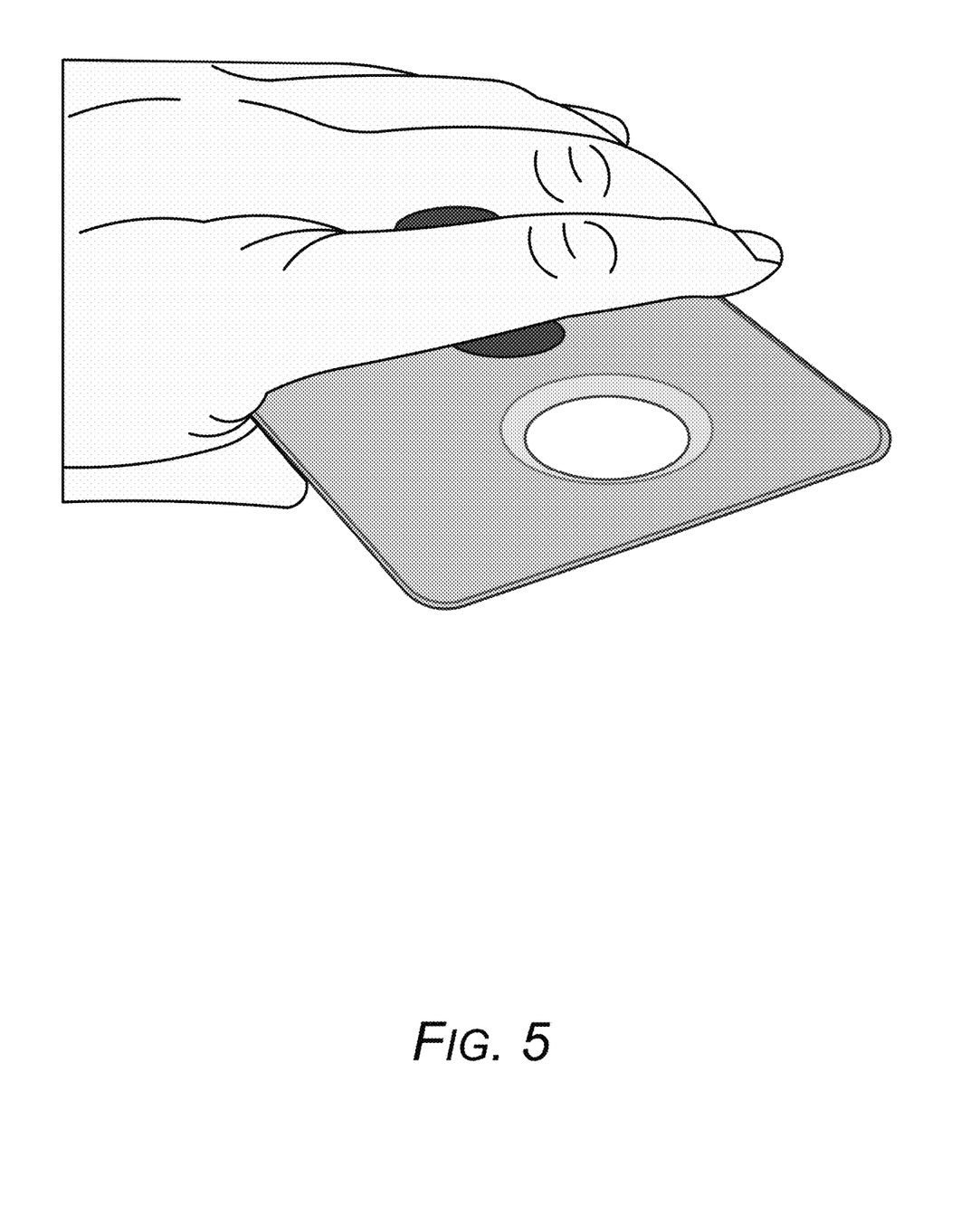
FIG. 5 illustrates an example deployable platform in operation, in accordance with one or more embodiments.

In operation, the deployable platform can utilize its optical sensors to measure a variety of conditions including, by way of example and not limitation, heart rate, blood oxygen, blood pressure, temperature, and the like. The deployable platform conveniently collapses into a recessed well so that it is safely stowed when it is not in use. When deployed, the deployable platform provides an ability to line up the optical sensors with a finger side artery, as represented in FIG. 5. In the illustrated and described embodiments, the user is able to securely carry the deployable platform and corresponding mobile communication device securely by scissor-gripping the deployable platform between two fingers, thus preventing accidental phone drops during diagnostic information collection. Although not illustrated, the modular attachment can include a table stand such that the mobile communication device can be placed on a table and pointed toward the user in landscape mode. This can allow a user to engage the deployable platform while seated at a table. The rotating nature of the deployable platform allows the deployable platform to be conveniently directed toward the user to facilitate measurements such as temperature sensing and the like.

Figure 7:
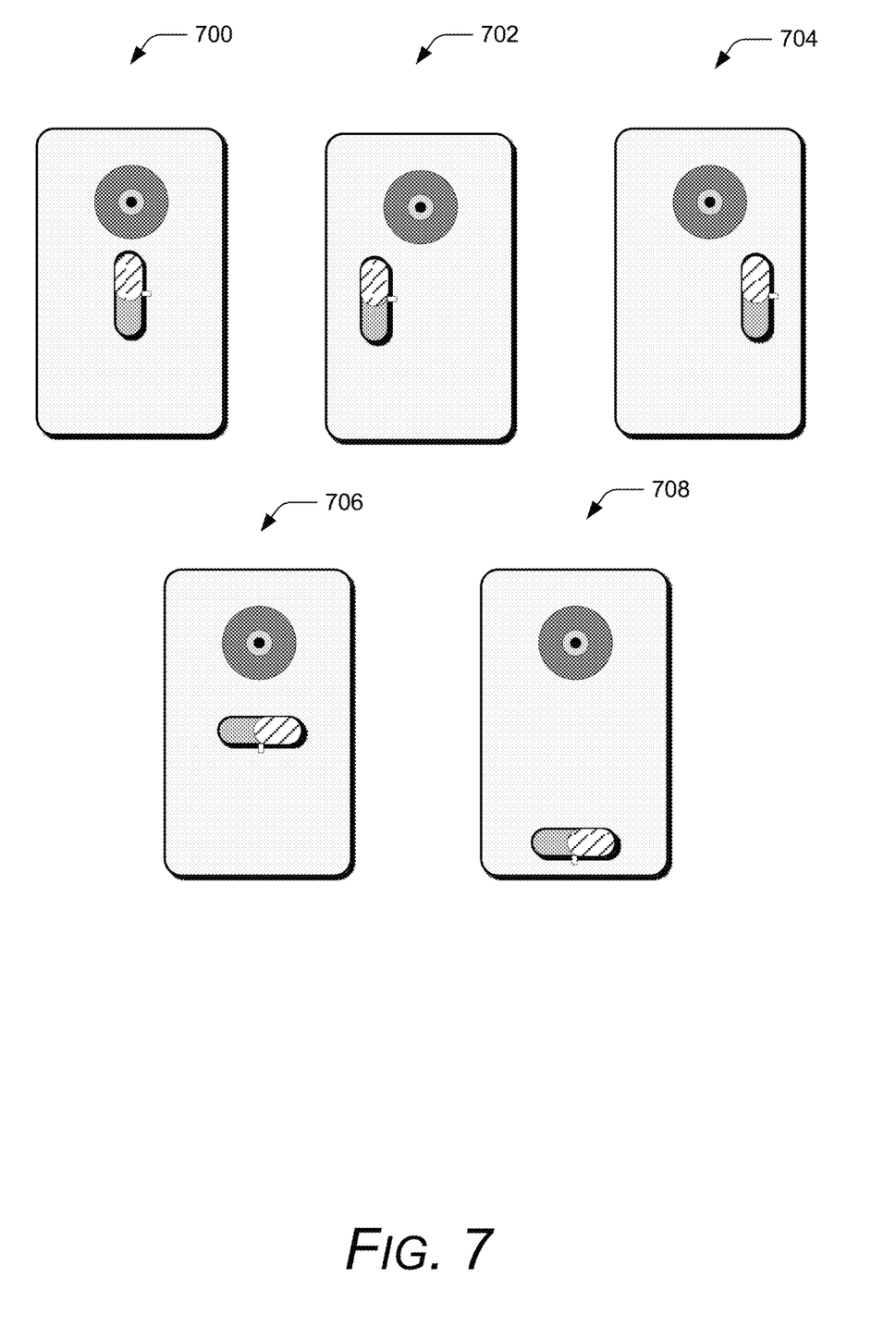
FIG. 7 illustrates several different embodiments in which the deployable platform can be mounted at different locations.

FIG. 7 illustrates various embodiments in which the deployable platform can be located in different locations on either the mobile communication device or the modular attachment. For example, as illustrated at 700, the deployable platform can be located in the middle of the mobile communication device or modular attachment. In this arrangement, the deployable platform is positioned along the central long axis of the mobile communication device or modular attachment. Illustrated at 702, the deployable platform can be located to the left of the central axis of the mobile communication device or modular attachment. Similarly, illustrated at 704, the deployable platform can be located to the right of the central axis of the mobile communication device or modular attachment Illustrated at 706, the deployable platform can be rotated 90 degrees so that the well in which the deployable platform is received extends transverse the central axis of the mobile communication device or modular attachment. Illustrated at 708, the deployable platform is located near the bottom of the mobile communication device or modular attachment. Needless to say, the examples of FIG. 7 serve as examples only, at various locations at which the deployable platform can be located. Accordingly, any suitable location can be utilized without departing from the spirit and scope of the claimed subject matter.

Having considered various locations at which the deployable platform can be located, consider now an example method in accordance with one or more embodiments.

Example Method

Figure 8:
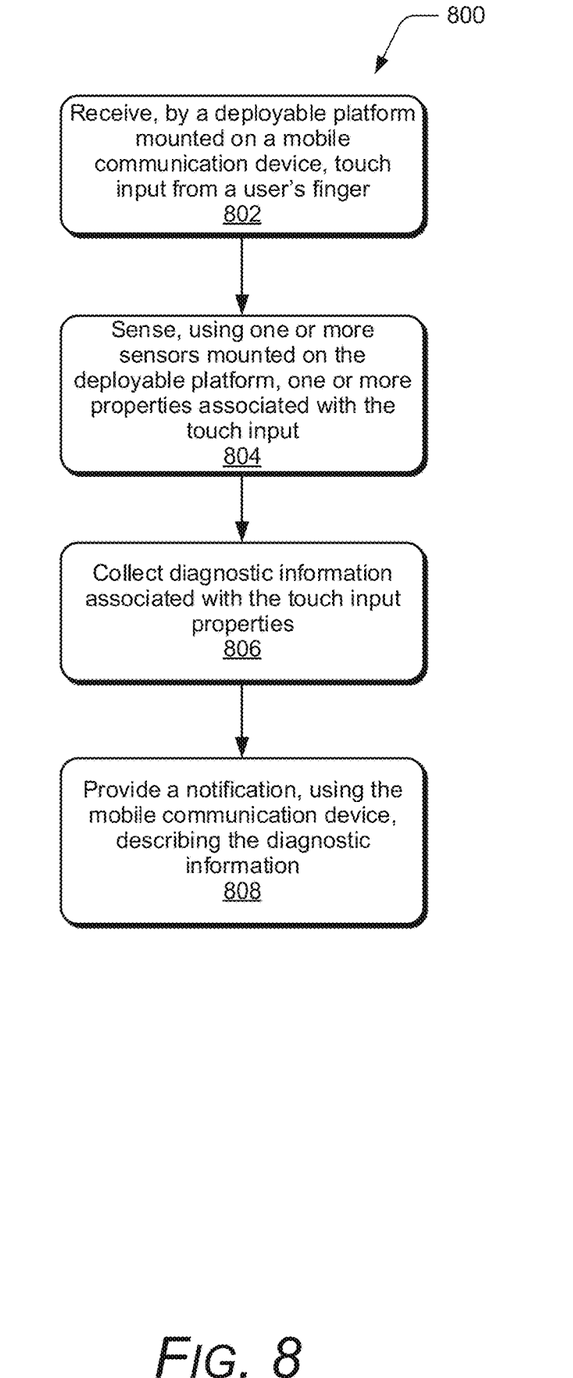
FIG. 8 is a flow diagram that illustrates operations in accordance with one or more embodiments.

FIG. 8 illustrates an example method 800 that employs techniques to sense and collect a user's diagnostic information, in connection with a mobile communication device, in accordance with one or more embodiments. Generally, any services, components, modules, methods, and/or operations described herein can be implemented using software, firmware, hardware (e.g., fixed logic circuitry), manual processing, or any combination thereof. Some operations of the example methods may be described in the general context of executable instructions stored on computer-readable storage memory that is local and/or remote to a computer processing system, and implementations can include software applications, programs, functions, and the like. Alternately or in addition, any of the functionality described herein can be performed, at least in part, by one or more hardware logic components, such as, and without limitation, Field-programmable Gate Arrays (FPGAs), Application-specific Integrated Circuits (ASICs), Application-specific Standard Products (ASSPs), System-on-a-chip systems (SoCs), Complex Programmable Logic Devices (CPLDs), and the like. The order in which the method is described is not intended to be construed as a limitation, and any number or combination of the described method operations can be performed in any order to perform a method, or an alternate method.

At 802, touch input from a user's finger is received by a deployable platform mounted on a mobile communication device. In one or more embodiments, the deployable platform includes multiple sensors, at least some of which are optical sensors, that are configured to enable diagnostic information regarding the user to be collected. Any suitable sensors can be utilized including, by way of example and not limitation, blood pressure sensors, temperature sensors, heart rate sensors, respiration sensors, blood oxygen sensors, and the like. In at least some embodiments, the deployable platform can be an integral part of the mobile communication device. That is, the deployable platform can comprise part of the mobile communication device as it is manufactured and sold. In at least some other embodiments, the deployable platform can be part of a modular attachment that is connected to the mobile communication device. The modular attachment can be connected at any suitable location on the mobile communication device. In at least some embodiments, the modular attachment is mounted to the backside of the mobile communication device and may be held in place by magnetic coupling elements. When so mounted, components within the modular attachment can communicate with components of the mobile communication device through a suitably-configured hardware interface.

At 804, one or more properties associated with the touch input are sensed using one or more sensors mounted on the deployable platform. Any suitable property or properties can be sensed by any suitable type of sensors. For example, properties can include, by way of example and not limitation, arterial occlusion, temperature, pulse wave velocities, and various other properties.

At 806, diagnostic information associated with the touch input properties are collected. The diagnostic information can include blood pressure, temperature, heart and respiration rates, blood oxygen levels, and the like.

At 808, a notification describing the diagnostic information is provided using the mobile communication device. The notification can include any suitable type of information that might be useful for a user. For example, the notification may simply inform the user of factual information associated with analysis of the diagnostic information, such as the user's blood pressure. Alternately or additionally, the notification may include further information such as diagnostic information, remedial information, or recommendations such as a recommendation to seek further medical assistance as a follow-up.

The notification can be a visual notification that is displayed by the mobile communication device. Alternately or additionally, the notification can be an audible notification. In embodiments, the notification can be provided directly by the mobile communication device itself or components of or associated with the mobile communication device. In other embodiments, the notification can be provided by receiving information from a third-party provider and providing a notification that includes the information provided by the third-party provider.

Having considered an example method in accordance with one or more embodiments, consider now an example computing device that can implement the embodiments described above.

Example Device

Figure 9:
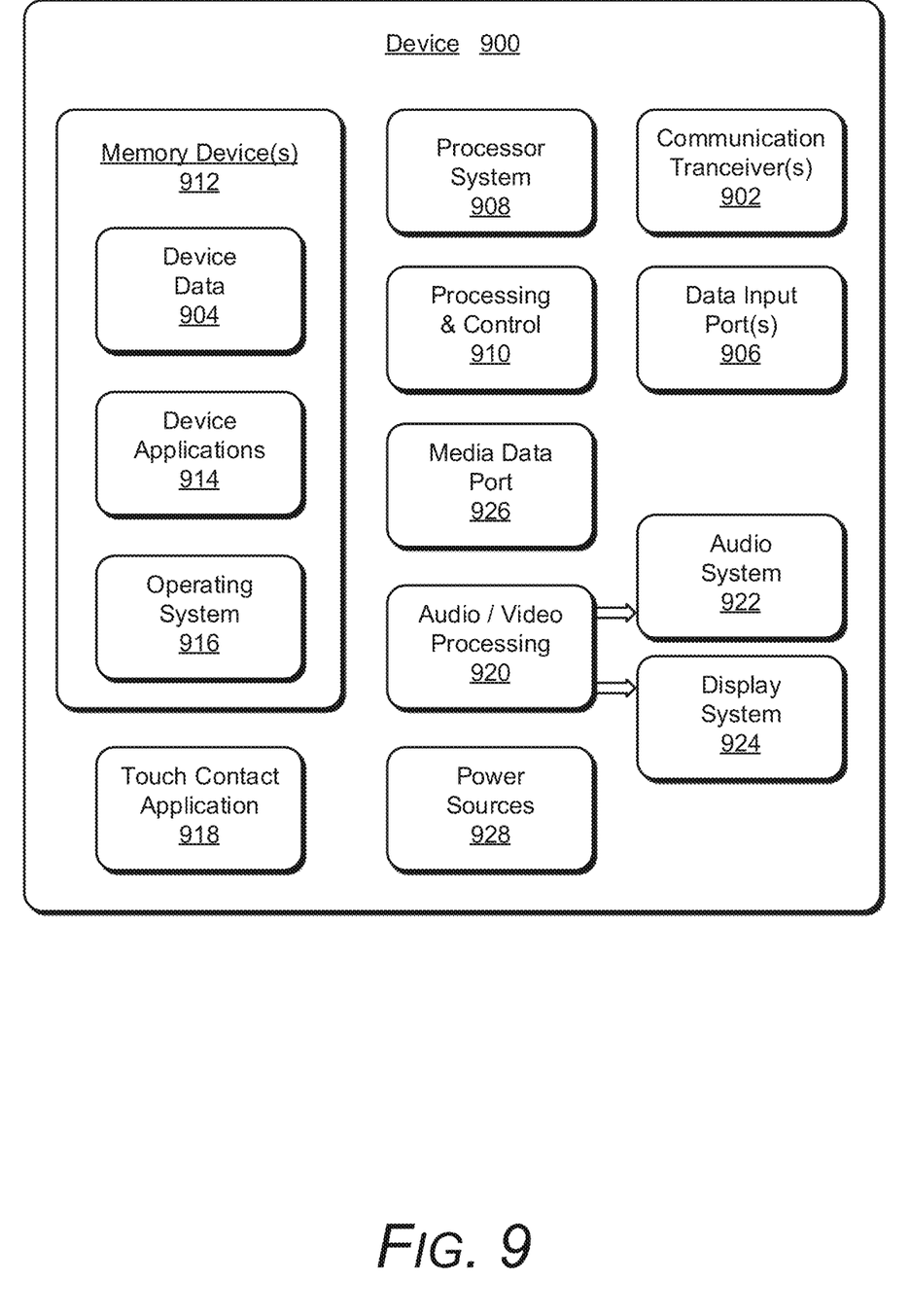
FIG. 9 illustrates various components of an example device that can implement various embodiments.

FIG. 9 illustrates various components of an example mobile communication device 900 in which diagnostic information can be sensed and collected in accordance with one or more embodiments. The example device 900 can be implemented as any suitable type of computing device, such as any type of client device, mobile phone, tablet, computing, communication, entertainment, gaming, media playback, and/or other type of device such as those mentioned above. For example, the device 120 shown in FIG. 1 may be implemented as the example device 900.

The device 900 includes communication transceivers 902 that enable wired and/or wireless communication of device data 904 with other devices. Additionally, the device data can include any type of audio, video, and/or image data. Example transceivers include wireless personal area network (WPAN) radios compliant with various IEEE 802.15 (Bluetooth™) standards, wireless local area network (WLAN) radios compliant with any of the various IEEE 802.11 (WiFi™) standards, wireless wide area network (WWAN) radios for cellular phone communication, wireless metropolitan area network (WMAN) radios compliant with various IEEE 802.15 (WiMAX™) standards, and wired local area network (LAN) Ethernet transceivers for network data communication.

The device 900 may also include one or more data input ports 906 via which any type of data, media content, and/or inputs can be received, such as user-selectable inputs to the device, messages, music, television content, recorded content, and any other type of audio, video, and/or image data received from any content and/or data source. The data input ports may include USB ports, coaxial cable ports, and other serial or parallel connectors (including internal connectors) for flash memory, DVDs, CDs, and the like. These data input ports may be used to couple the device to any type of components, peripherals, or accessories such as microphones and/or cameras.

The device 900 includes a processing system 908 of one or more processors (e.g., any of microprocessors, controllers, and the like) and/or a processor and memory system implemented as a system-on-chip (SoC) that processes computer-executable instructions. The processor system may be implemented at least partially in hardware, which can include components of an integrated circuit or on-chip system, an application-specific integrated circuit (ASIC), a field-programmable gate array (FPGA), a complex programmable logic device (CPLD), and other implementations in silicon and/or other hardware. Alternatively, or in addition, the device can be implemented with any one or combination of software, hardware, firmware, or fixed logic circuitry that is implemented in connection with processing and control circuits, which are generally identified at 910. Processor system 908 can also include various sensors such as those described above. The device 900 may further include any type of a system bus or other data and command transfer system that couples the various components within the device. A system bus can include any one or combination of different bus structures and architectures, as well as control and data lines.

The device 900 also includes computer-readable storage memory or memory devices 912 that enable data storage, such as data storage devices that can be accessed by a computing device, and that provide persistent storage of data and executable instructions (e.g., software applications, programs, functions, and the like). Examples of the computer-readable storage memory 912 include volatile memory and non-volatile memory, fixed and removable media devices, and any suitable memory device or electronic data storage that maintains data for computing device access. The computer-readable storage memory can include various implementations of random access memory (RAM), read-only memory (ROM), flash memory, and other types of storage media in various memory device configurations. The device 900 may also include a mass storage media device. The device 900 may also make use of network-based storage, such as that available through various cloud-based services.

The computer-readable storage memory provides data storage mechanisms to store the device data 904, other types of information and/or data, and various device applications 914 (e.g., software applications). For example, an operating system 916 can be maintained as software instructions with a memory device and executed by the processing system 908. The device applications may also include a device manager, such as any form of a control application, software application, signal-processing and control module, code that is native to a particular device, a hardware abstraction layer for a particular device, and so on. In this example, the device 900 includes a touch contact application 918.

The device 900 also includes an audio and/or video processing system 920 that generates audio data for an audio system 922 and/or generates display data for a display system 924. The audio system and/or the display system may include any devices that process, display, and/or otherwise render audio, video, display, and/or image data. Display data and audio signals can be communicated to an audio component and/or to a display component via an RF (radio frequency) link, S-video link, HDMI (high-definition multimedia interface), composite video link, component video link, DVI (digital video interface), analog audio connection, or other similar communication link, such as media data port 926. In implementations, the audio system and/or the display system are integrated components of the example device. Alternatively, the audio system and/or the display system are external, peripheral components to the example device.

The device 900 can also include one or more power sources 928, such as when the device is implemented as a mobile device. The power sources may include a charging and/or power system, and can be implemented as a flexible strip battery, a rechargeable battery, a charged super-capacitor, and/or any other type of active or passive power source.

Conclusion

Various embodiments provide a mobile communication device to sense and collect a user's diagnostic information. Diagnostic information is automatically collected by the mobile communication device where it can be processed locally and/or provided or otherwise transmitted, by way of a suitably-configured network, to one or more third-party service providers for further diagnostic analysis.

The mobile communication device can include a variety of sensors to measure various diagnostic information associated with the user. These sensors can include, by way of example and not limitation, heart rate sensors, blood oxygen sensors, blood pressure sensors, temperature sensors, and the like. In operation, the sensors are located on a deployable platform located on the back of the mobile communication device. The deployable platform is rotatably mounted relative to the mobile communication device and is rotatable from an undeployed or stowed position, to a deployed position. In the undeployed or stowed position, the deployable platform is received within a recessed well that is sized to ensure that the deployable platform is protected from things such as inadvertent snags and the like. In the deployed position, the deployable platform is rotated out of the recessed well to extend generally away from the mobile communication device. When in the deployed position, the deployable platform can be engaged by a user, as by being placed against the user's finger, so that the sensors on the deployable platform can collect diagnostic information associated with the user.

Although various embodiments have been described in language specific to features and/or methods, the subject of the appended claims is not necessarily limited to the specific features or methods described. Rather, the specific features and methods are disclosed as example implementations, and other equivalent features and methods are intended to be within the scope of the appended claims. Further, various different embodiments are described and it is to be appreciated that each described embodiment can be implemented independently or in connection with one or more other described embodiments.

The invention claimed is:

1. A method for sensing and collecting diagnostic information of a user of a mobile device, the method comprising:
receiving a touch input on one or more sensors of a deployable sensor platform integrated with the mobile device, the deployable sensor platform being configurable to move from a recessed position in which the one or more sensors are stowed preventing contact with the one or more sensors to an exposed position in which the user can place the deployable sensor platform between two fingers enabling the touch input on the one or more sensors;
sensing one or more vital signs of the user from sensor data obtained by the one or more sensors of the deployable sensor platform responsive to the touch input;
analyzing the sensor data as diagnostic information to determine one or more fitness properties of the user; and
providing a notification to report the diagnostic information as the one or more fitness properties of the user.

2. The method as recited in claim 1, wherein the one or more sensors of the deployable sensor platform includes at least one of an optical sensor, a blood pressure sensor, a temperature sensor, a heart rate sensor, or a blood oxygen sensor.

3. The method as recited in claim 1, wherein the deployable sensor platform is one of integrated into a housing of the mobile device, or integrated into a modular component that attaches to the mobile device.

4. The method as recited in claim 1, wherein the deployable sensor platform is rotatable from the recessed position to the exposed position.

5. The method as recited in claim 1, wherein the one or more sensors of the deployable sensor platform are configured to obtain the sensor data in the exposed position of the deployable sensor platform.

6. The method as recited in claim 1, wherein the user can place respective sides of the two fingers against the one or more sensors in the exposed position of the deployable sensor platform.

7. The method as recited in claim 1, wherein the one or more sensors of the deployable sensor platform includes multiple sensors comprising a blood pressure sensor, a temperature sensor, a heart rate sensor, and a blood oxygen sensor.

8. The method as recited in claim 1, wherein the deployable sensor platform comprises a modular attachment that is configured to attach to the mobile device.

9. A mobile device comprising:
a deployable sensor platform integrated with the mobile device, the deployable sensor platform configurable to move from a recessed position in which one or more sensors are stowed preventing contact with the one or more sensors to an exposed position in which a user can place the deployable sensor platform between two fingers enabling a touch input on the one or more sensors;
a controller implemented at least partially in computer hardware to:
receive sensor data associated with one or more vital signs of the user from the one or more sensors on the deployable sensor platform configured in the exposed position;
analyze the sensor data to determine one or more fitness properties of the user; and
initiate a notification to report the one or more fitness properties.

10. The mobile device as recited in claim 9, wherein the one or more sensors of the deployable sensor platform are optical sensors.

11. The mobile device as recited in claim 10, wherein the one or more optical sensors comprises at least one of a blood pressure sensor, a temperature sensor, a heart rate sensor, or a blood oxygen sensor.

12. The mobile device as recited in claim 9, wherein the deployable sensor platform is one of integrated into a housing of the mobile device, or integrated into a modular component that attaches to the mobile device.

13. The mobile device as recited in claim 9, wherein the user can place respective sides of the two fingers against the one or more sensors in the exposed position of the deployable sensor platform.

14. The mobile device as recited in claim 9, wherein the one or more sensors of the deployable sensor platform includes multiple sensors comprising a blood pressure sensor, a temperature sensor, a heart rate sensor, and a blood oxygen sensor.

15. A mobile device comprising:
a modular attachment configured to attach to the mobile device, the modular attachment including a deployable sensor platform configurable to move from a recessed position within the modular attachment in which one or more sensors are stowed preventing contact with the one or more sensors to an exposed position in which the user can place the deployable sensor platform between two fingers enabling a touch input on the one or more sensors;
a controller implemented at least partially in computer hardware to:
receive sensor data associated with one or more vital signs of the user from the one or more sensors on the deployable sensor platform configured in the exposed position in which the one or more sensors are exposed enabling the touch input;
analyze the sensor data to determine one or more fitness properties of the user; and
initiate a notification to report the one or more fitness properties.

16. The mobile device as recited in claim 15, wherein the one or more sensors of the deployable sensor platform includes at least one of an optical sensor, a blood pressure sensor, a temperature sensor, a heart rate sensor, or a blood oxygen sensor.

17. The mobile device as recited in claim 15, wherein the deployable sensor platform is rotatable from the recessed position to the exposed position.

18. The mobile device as recited in claim 15, wherein the controller is implemented to receive the sensor data from the one or more sensors on the deployable sensor platform rotated to the exposed position of the deployable sensor platform.

19. The mobile device as recited in claim 15, wherein the user can place respective sides of the two fingers against the one or more sensors in the exposed position of the deployable sensor platform.

20. The mobile device as recited in claim 15, wherein the one or more sensors of the deployable sensor platform includes multiple sensors comprising a blood pressure sensor, a temperature sensor, a heart rate sensor, and a blood oxygen sensor.

* * * * *